(12) United States Patent
Schmitt et al.

(10) Patent No.: US 8,160,895 B2
(45) Date of Patent: Apr. 17, 2012

(54) USER INTERFACE FOR CLINICAL DECISION SUPPORT

(75) Inventors: Michael D. Schmitt, Kansas City, MO (US); Keith A. Huffman, Lee's Summit, MO (US); Leo V. Perez, Platte City, MO (US); J. Christopher Murrish, Overland Park, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 1215 days.

(21) Appl. No.: 11/623,589

(22) Filed: Jan. 16, 2007

(65) Prior Publication Data

US 2008/0082357 A1 Apr. 3, 2008

Related U.S. Application Data

(60) Provisional application No. 60/827,594, filed on Sep. 29, 2006.

(51) Int. Cl.
*G06Q 10/00* (2012.01)
*G06Q 50/00* (2012.01)
(52) U.S. Cl. .................................. 705/2; 705/3
(58) Field of Classification Search .................. 705/2–3; 707/5; 715/781
See application file for complete search history.

(56) References Cited

U.S. PATENT DOCUMENTS

| | | | |
|---|---|---|---|
| 5,772,585 A | 6/1998 | Lavin | |
| 6,983,423 B2 * | 1/2006 | Dvorak et al. | 715/781 |
| 7,275,220 B2 | 9/2007 | Brummel et al. | |
| 2001/0050610 A1 | 12/2001 | Gelston | |
| 2001/0050810 A1 | 12/2001 | Lorincz | |
| 2002/0042726 A1 | 4/2002 | Mayaud | |
| 2002/0091687 A1 * | 7/2002 | Eglington | 707/5 |
| 2003/0110059 A1 * | 6/2003 | Janas et al. | 705/2 |
| 2003/0163348 A1 | 8/2003 | Stead et al. | |
| 2004/0210548 A1 | 10/2004 | Ketcherside et al. | |
| 2004/0260666 A1 | 12/2004 | Pestotnik | |
| 2007/0112782 A1 | 5/2007 | Lobach et al. | |
| 2008/0015894 A1 | 1/2008 | Miller | |

OTHER PUBLICATIONS

"How Should We Make the Admission Decision in Community-Acquired Pneumonia", Dominik Aronsky, MD, PhD, and Nathan C. Dean, MD, Medical Clinics of North America, vol. 85, Issue 6, Nov. 1, 2001, pp. 1397-1411.*
Non-Final Office Action mailed Jul. 8, 2009 re U.S. Appl. No. 11/623,584, filed Jan. 16, 2007.
Non-Final Office Action mailed Jul. 21, 2009 re U.S. Appl. No. 12/246,280, filed Oct. 6, 2008.
Final Office Action mailed Jan. 29, 2010, U.S. Appl. No. 12/246,280, filed Oct. 6, 2008, 17 pages.

(Continued)

*Primary Examiner* — Luke Gilligan
*Assistant Examiner* — Joseph Burgess
(74) *Attorney, Agent, or Firm* — Shook, Hardy & Bacon L.L.P.

(57) ABSTRACT

User interfaces for proactive and interactive clinical decision support events are provided. When a clinical decision support event is initiated for a patient, relevant stored clinical information associated with the patient is accessed. A user interface is generated using the stored clinical information. A clinician may interact with the user interface by providing user-provided clinical information that may add to and/or modify the stored clinical information in the user interface. Clinical advice is provided via the user interface based on the stored clinical information and the user-provided clinical information.

15 Claims, 11 Drawing Sheets

OTHER PUBLICATIONS

The Source (web based software); VISICU, Inc., 217 E. Redwood Street, Suite 1900, Baltimore, MD 21202; www.visicu.com.

Final Office Action mailed Dec. 7, 2010 re U.S. Appl. No. 11/623,592.

Final Office Action mailed Jan. 6, 2010 re U.S. Appl. No. 11/623,584, filed Jan. 16, 2007.

Non-Final Office Action mailed Apr. 27, 2010 re U.S. Appl. No. 11/623,592, filed Jan. 16, 2007.

Final Office Action mailed Aug. 30, 2011 re U.S. Appl. No. 12/246,280, filed Oct. 6, 2008.

Non-Final Office Action mailed Mar. 16, 2011 re U.S. Appl. No. 12/246,280, filed Oct. 6, 2008.

* cited by examiner

B-CELL DEFICIENCY

PATIENT NAME: CALIMAN, BARNEY
LOCATION: 4 NORTH – ICU  404
SEX: MALE
AGE: 83 YEARS
HEIGHT: 6.14 FT / 187 CM
WEIGHT: 171.91 LB / 78 KG

| SYMPTOMS INDICATING B-CELL-DEFICIENCY | CLINICAL INFORMATION | CRITERIA MET |
|---|---|---|
| PERSISTANT, RECURRENT OR SERVER BACTERIAL INFECTIONS | ○ YES ● NO | NO |
| LOW SERUM IMMUNOGLOBULIN LEVELS | ● YES ○ NO | NO |
| FAMILY HISTORY OF XLA, HIGM, OR CVID OR OF RECURRENT, SEVERE INFECTIONS | ○ YES ● NO | NO |

| SPECIFIC SYMPTOMS | CLINICAL INFORMATION | CRITERIA MET |
|---|---|---|
| SERUM LEVELS OF IgA | 300  01/10/06 11:01:39 | YES |
| SERUM LEVELS OF IgG | 387  01/10/06 11:01:39 | YES |
| SERUM LEVELS OF IgM | 400  01/10/06 11:39:14 | YES |
| PARTIAL Ig AND B-CELL-DEFICIENCY PHENOTYPES | RESULT NOT FOUND | NO |
| B-CELL COUNT | RESULT NOT FOUND | NO |
| T-CELL COUNT | RESULT NOT FOUND | NO |
| ONSET OF SYMPTOMS IN OLDER PATIENTS | ○ YES ● NO | NO |
| ENLARGED LYMPH NODES AND TONSILS | ○ YES ● NO | NO |
| ABSENT OR VERY SMALL TONSILS AND ADENOID TISSUE | ○ YES ● NO | NO |
| OPPORTUNISTIC INFECTIONS | ○ YES ● NO | NO |
| MALE-LIMITED FAMILY HISTORY | ○ YES ● NO | NO |
| EXCLUSION OF OTHER CAUSES OF ANTIBODY DEFICIENCY | ○ YES ● NO | NO |
| UNDETECTABLE OR LOW SERUM Ig LEVELS | ● YES ○ NO | YES |

BASED ON THE ABOVE CRITERIA, THE FOLLOWING TEST(S) ARE RECOMMENDED: NONE

ADD ORDER FOR:
☐ AICDA
☐ UNG
☐ CD40 (TNRFSF5)
☐ BTK
☐ TNFRSF13B (TACI)

[DONE]

FIG. 4A.

B-CELL DEFICIENCY

| PATIENT NAME: CALIMAN, BARNEY | SEX: MALE | HEIGHT: 6.14 FT / 187 CM |
| LOCATION: 4 NORTH – ICU, 404 | AGE: 83 YEARS | WEIGHT: 171.91 LB /78KG |

| SYMPTOMS INDICATING B-CELL-DEFICIENCY | CLINICAL INFORMATION | | CRITERIA MET |
| --- | --- | --- | --- |
| PERSISTANT, RECURRENT OR SERVER BACTERIAL INFECTIONS | ○ YES ⊙ NO | | NO |
| LOW SERUM IMMUNOGLOBULIN LEVELS | ⊙ YES ○ NO | | YES |
| FAMILY HISTORY OF XLA, HIGM, OR CVID OR OF RECURRENT, SEVERE INFECTIONS | ○ YES ⊙ NO | | NO |
| SPECIFIC SYMPTOMS | CLINICAL INFORMATION | | CRITERIA MET |
| SERUM LEVELS OF IgA | 300 | 01/10/06 11:01:39 | YES |
| SERUM LEVELS OF IgG | 387 | 01/10/06 11:01:39 | YES |
| SERUM LEVELS OF IgM | 400 | 01/10/06 11:39:14 | YES |
| PARTIAL Ig- AND B-CELL-DEFICIENCY PHENOTYPES | | RESULT NOT FOUND | NO |
| B-CELL COUNT | | RESULT NOT FOUND | NO |
| T-CELL COUNT | | RESULT NOT FOUND | NO |
| ONSET OF SYMPTOMS IN OLDER PATIENTS | ⊙ YES ○ NO | | YES |
| ENLARGED LYMPH NODES AND TONSILS | ○ YES ⊙ NO | | NO |
| ABSENT OR VERY SMALL TONSILS AND ADENOID TISSUE | ○ YES ⊙ NO | | NO |
| OPPORTUNISTIC INFECTIONS | ○ YES ⊙ NO | | NO |
| MALE-LIMITED FAMILY HISTORY | ○ YES ⊙ NO | | NO |
| EXCLUSION OF OTHER CAUSES OF ANTIBODY DEFICIENCY | ○ YES ⊙ NO | | NO |
| UNDETECTABLE OR LOW SERUM Ig LEVELS | ⊙ YES ○ NO | | YES |

BASED ON THE ABOVE CRITERIA, THE FOLLOWING TEST(S) ARE RECOMMENDED: AICDA (HIGM2), UNG

ADD ORDER FOR:
☒ AICDA
☒ UNG
☐ CD40 (TNRSF5)
☐ BTK
☐ TNFRSF13B (TACI)

[ DONE ]

FIG. 4B.

XIGRIS

PATIENT: ROBBINS, IDA VIOLET  AGE: 84 YEARS  HEIGHT: 5.09FT / 155CM  WEIGHT: 99.18LB / 45KG

506 → RECOMMENDATION: DO NOT ORDER XIGRIS. PATIENT DOES NOT MEET CRITERIA AS DEFINED.

| CRITERIA | CLINICAL INFORMATION | | CRITERIA MET |
|---|---|---|---|
| 1) PATIENT HAS KNOWN OR SUSPECTED INFECTION (1 OF THE FOLLOWING): | | | |
| DOES PATIENT HAVE WBC'S IN A NORMALLY STERILE BODY FLUID OR POSITIVE BLOOD CULTURES? | ○ YES ⊙ NO | | NO |
| DOES PATIENT HAVE A PERFORATED VISCUS? | ○ YES ⊙ NO | | NO |
| IS THERE CXR EVIDENCE OF PNEUMONIA WITH PURULENT SPUTUM PRODUCTION? | ○ YES ⊙ NO | | NO |
| DOES PATIENT HAVE A SYNDROME WITH A HIGH RISK OF ASSOCIATED INFECTION? | ○ YES ⊙ NO | | NO |
| 2) PATIENT HAS SYSTEMIC INFLAMMATORY RESPONSE SYNDROME (SIRS) CRITERIA (3 OF THE FOLLOWING): | | | |
| CORE BODY TEMP < 36 C OR > DEGREES C | 38.2 | 02/14/05 13:39:00 | YES |
| HEART RATE > 90BPM | 120 | 02/17/05 13:25:00 | YES |
| DOES THIS PATIENT HAVE A CONDITION KNOWN TO INCREASE HEART RATE OR ON TREATMENTS WHICKH MAY PREVENT TACHYCARDIA? | ○ YES ○ NO | | |
| RESPIRATORY RATE ≥ 20 BREATHS/MIN | 22 | 02/17/05 13:30:00 | YES |
| OR PaCo2 OF < 32 mmHg | | | |
| OR ON MECHANICAL VENTILLATION | ○ YES ○ NO | | |
| WBC < 4 OR > 12 MCG/L | 5.0 | 02/16/05 15:04:00 | YES |
| OR > 10% BANDS ON DIFFERENTIAL | 11 | 02/16/05 16:01:00 | |
| 3) EVIDENCE OF ORGAN DYSFUNCTION PRESENT FOR LESS THAN 48 HOURS (2 OF THE FOLLOWING): | | | |
| CARDIOVASCULAR SYSTEM DYSFUNCTION | | | YES |
| SBP ≤ 90 | 88 | 02/17/05 13:25:00 | |
| OR MAP < 70 mmHg FOR 1 HOUR | 69 | 02/17/05 13:25:00 | |
| DOES THE PATIENT HAVE ADEQUATE FLUID RESUSCITATION ADEQUATE VOLUME OR USAGE OF VASOPRESSORS? | ○ YES ○ NO | | |
| RENAL DYSFUNCTION | | | NO |
| URINE OUTPUT < 0.5ML/KG/HR FOR 1 HOUR | ○ YES ○ NO | | |
| DOES THE PATIENT HAVE ADEQUATE FLUID RESUSCITATION | ○ YES ○ NO | | |
| RESPIRATORY SYSTEM DYSFUNCTION | | | NO |
| PaO2/FiO2 RATIO < 250 | | | |
| HEMATALOGIC DYSFUNCTION | | | YES |
| PLATELET COUNT < 80,000 | 30000 | 02/21/05 17:28:00 | |
| OR HAS THE PATIENT HAD A 50% DECREASE IN PLATELETS IN THE PREVIOUS 3 DAYS? | ○ YES ○ NO | | |
| UNEXPLAINED METABOLIC ACIDOSIS | | | YES |
| Ph ≤ 7.30 | 7.30 | 02/17/05 11:00:00 | |
| OR A BASE DEFICIT OF ≥ 5 | | | |
| WITH A PLASMA LACTATE LEVEL > 1.5X THE UPPER LIMIT OF NORMAL | | | |

ALERT ACTION
⊙ CANCEL XIGRIS ORDER
○ CONTINUE ORDERING XIGRIS

FIG. 5A.

XIGRIS

PATIENT: ROBBINS, IDA VIOLET  AGE: 84 YEARS  HEIGHT: 5.09FT / 155CM  WEIGHT: 99.18LB / 45KG

506 → RECOMMENDATION: CRITERIA MET FOR XIGRIS ORDER; PLEASE CONTINUE BY VERIFYING THAT NO CONTRAINDICATIONS ARE PRESENT.

| CRITERIA | CLINICAL INFORMATION | CRITERIA MET |
|---|---|---|
| 1) PATIENT HAS KNOWN OR SUSPECTED INFECTION (1 OF THE FOLLOWING): | | |
| DOES PATIENT HAVE WBC'S IN A NORMALLY STERILE BODY FLUID OR POSITIVE BLOOD CULTURES? | ○ YES ● NO | NO |
| DOES PATIENT HAVE A PERFORATED VISCUS? | ○ YES ● NO | NO |
| IS THERE CXR EVIDENCE OF PNEUMONIA WITH PURULENT SPUTUM PRODUCTION? | ○ YES ● NO | NO |
| DOES PATIENT HAVE A SYNDROME WITH A HIGH RISK OF ASSOCIATED INFECTION? | ● YES ○ NO | YES |
| 2) PATIENT HAS SYSTEMIC INFLAMMATORY RESPONSE SYNDROME (SIRS) CRITERIA (3 OF THE FOLLOWING): | | |
| CORE BODY TEMP < 36 C OR > DEGREES C | 38.2    03/14/05 13:39:00 | YES |
| HEART RATE > 90BPM | 120    02/17/05 13:25:00 | YES |
| DOES THIS PATIENT HAVE A CONDITION KNOWN TO INCREASE HEART RATE OR ON TREATMENTS WHICH MAY PREVENT TACHYCARDIA? | ○ YES ● NO | |
| RESPIRATORY RATE ≥ 20 BREATHS/MIN | 22    02/17/05 13:30:00 | YES |
| OR PaCo2 OF < 32 mmHg | | |
| OR ON MECHANICAL VENTILATION | ○ YES ○ NO | |
| WBC < 4 OR > 12 MCG/L | 5.0    02/16/05 15:04:00 | YES |
| OR > 10% BANDS ON DIFFERENTIAL | 11    02/16/05 16:01:00 | |
| 3) EVIDENCE OF ORGAN DYSFUNCTION PRESENT FOR LESS THAN 48 HOURS (2 OF THE FOLLOWING): | | |
| CARDIOVASCULAR SYSTEM DYSFUNCTION | | YES |
| SBP ≤ 90 | 88    02/17/05 13:25:00 | |
| OR MAP < 70 mmHg FOR 1 HOUR | 69    02/17/05 13:25:00 | |
| DOES THE PATIENT HAVE ADEQUATE FLUID RESUSCITATION ADEQUATE VOLUME OR USAGE OF VASOPRESSORS? | ○ YES ● NO | |
| RENAL DYSFUNCTION | | NO |
| URINE OUTPUT < 0.5ML/KG/HR FOR 1 HOUR | ○ YES ○ NO | |
| DOES THE PATIENT HAVE ADEQUATE FLUID RESUSCITATION? | ○ YES ○ NO | |
| RESPIRATORY SYSTEM DYSFUNCTION | | |
| PaO2/FiO2 RATIO < 250 | | |
| HEMATOLOGIC DYSFUNCTION | | YES |
| PLATELET COUNT < 80,000 | 30000   02/21/05 17:26:00 | |
| OR HAS THE PATIENT HAD A 50% DECREASE IN PLATELETS IN THE PREVIOUS 3 DAYS? | ○ YES ● NO | |
| UNEXPLAINED METABOLIC ACIDOSIS | | YES |
| Ph ≤ 7.30 | 7.30    02/17/05 11:00:00 | |
| OR A BASE DEFICIT OF ≥ 5 | | |
| WITH A PLASMA LACTATE LEVEL > 1.5X THE UPPER LIMIT OF NORMAL | | |

ALERT ACTION
○ CANCEL XIGRIS ORDER
● CONTINUE ORDERING XIGRIS

FIG. 5B.

PNEUMONIA SEVERITY INDEX

TRAPP, ROBERT JOHN HAS A PNEUMONIA SEVERITY INDEX OF 84

| CRITERIA | CLINICAL INFORMATION | | CRITERIA MET | POINTS ASSIGNED |
|---|---|---|---|---|
| AGE (YEARS) | 64 | | | +64 |
| RESPIRATORY RATE (> 30 BPM) | 20 | 03/14/05 15:43:00 | NO | +0 |
| SYSTOLIC BLOOD PRESSURE (<90 mmHg) | 120 | 03/14/05 14:37:00 | NO | +0 |
| APICAL HEART RATE (≥ 125 BPM) | 120 | 03/14/05 15:42:00 | NO | +0 |
| BUN (≥ 30 MG/DL) | 20 | 03/14/05 15:07:00 | NO | +0 |
| SODIUM (> 130 mmol/L) | 135 | 03/14/05 15:02:00 | NO | +0 |
| GLUCOSE LEVEL (≥ 250 MG/DL) | 100 | 03/14/05 15:32:00 | NO | +0 |
| pO2 ART (> 60 mmHg) | 65 | 03/14/05 15:02:00 | NO | +0 |
| TEMPERATURE (< 35° C OR > 40° C) | 37.1 | 03/15/05 15:08:00 | NO | +0 |
| pH ART (< 7.35) | 7.40 | 03/14/05 15:02:00 | NO | +0 |
| HEMATOCRIT (< 30%) | 25 | 03/16/05 08:58:08 | YES | +10 |
| PLEURAL EFFUSION | | | ○ YES ● NO | +0 |
| NEOPLASTIC DISEASE | | | ○ YES ● NO | +0 |
| LIVER DISEASE | | | ○ YES ● NO | +0 |
| CONGESTIVE HEART FAILURE | ACTIVE PROBLEM: CONGESTIVE HEART FAILURE | | ● YES ○ NO | +10 |
| RENAL DISEASE | | | ○ YES ● NO | +0 |
| ALTERED MENTAL STATUS | | | ○ YES ● NO | +0 |
| NURSING HOME RESIDENT | | | ○ YES ● NO | +0 |
| CEREBROVASCULAR DISEASE | | | ○ YES ● NO | +0 |

CALCULATED PNEUMONIA SEVERITY INDEX = 84

| PSI | CLASS | 30 DAY MORTALITY (%) | ORDER TO CONSIDER |
|---|---|---|---|
| < 71 | I - II | < 1 | CAP, AMBULATORY ORDER SET |
| 71 - 90 | III | < 2.8 | CAP, ADMIT MED SURG ORDER SET |
| 91 - 130 | IV | 8.5 – 9.3 | CAP, ADMIT TO ICU ORDER SET |
| > 130 | V | 27.0 – 31.1 | CAP, ADMIT TO ICU ORDER SET |

[ RESET ]  [ SAVE PSI TO CHART ]

[ DONE ]

FIG. 6A.

CAP – ADULT > CONDITION > PNEUMONIA PREDICTION RULE

CAP – ADULT > CONDITION > PNEUMONIA PREDICTION RULE

🖨 PRINT TOPICS ☐ INCLUDE SYNOPSIS

REMINDER:
FOR PATIENTS WITH COMMUNITY-ACQUIRED PNEUMONIA (CAP), CONSIDER APPLYING A VALIDATED PREDICTION RULE TO ASSIST IN THE ADMISSION DECISION.

RATIONALE:
IN A NONRANDOMIZED PROSPECTIVE STUDY, FINE ET AL (1997) DEVELOP THE PNEUMONIA SEVERITY INDEX (PSI), THE PREDICTION RULE THAT HAS BEEN DERIVED AND VALIDATED IN THE LARGEST COHORT OF PATIENTS WITH CAP. IN STEP 1 OF THE PREDICTION RULE, PATIENTS ARE ASSIGNED TO RISK CLASS I IF THEY ARE LESS THAN 50 YEARS OF AGE, IF THEY DO NOT HAVE A HISTORY OF CERTAIN COEXISTING CONDITIONS (NEOPLASTIC DISEASE, CONGESTIVE HEART FAILURE, CEREBROVASCULAR DISEASE, RENAL DISEASE, LIVER DISEASE), AND IF THEY DO NOT HAVE CERTAIN ABNORMALITIES ON PHYSICAL EXAMINATION (ALTERED MENTAL STATUSM PULSE GREATER THAN OR EQUAL TO 125/MINUTE, RESPIRATION RATE GREATER THAN OR EQUAL TO 30/MINUTE, SYSTOLIC BLOOD PRESSURE LESS THAN 90mm Hg, TEMPERATURE , 35 C OR > TO 40 C). SPECIFIC DETAILS OF STEP 2 OF THE PREDICTION RULE AND CHARACTERISTICS OF THE PSI SCORE WITH RECOMMENDATIONS SPECIFIC FOR EACH CLASS ARE PRESENTED BELOW.

POINT SCORING SYSTEM FOR STEP 2 OF THE PREDICTION RULE FOR ASSIGNMENT TO RISK CLASSES II, III, IV, V

| CHARACTERISTIC | POINTS ASSIGNED |
|---|---|
| DEMOGRAPHIC FACTOR | |
| AGE | |
| MEN | AGE (YEARS) |
| WOMEN | AGE (YEARS) -10 |
| NURSING HOME RESIDENT | +10 |
| COEXISTING ILLNESSES | |
| NEOPLASTIC DISEASE | +30 |
| LIVER DISEASE | +20 |

FIG. 6B.

PNEUMONIA SEVERITY INDEX

TRAPP, ROBERT JOHN HAS A PNEUMONIA SEVERITY INDEX OF 94

| CRITERIA | CLINICAL INFORMATION | | CRITERIA MET | POINTS ASSIGNED |
|---|---|---|---|---|
| AGE (YEARS) | 64 | | | +64 |
| RESPIRATORY RATE (> 30 BPM) | 20 | 03/14/05 15:43:00 | NO | +0 |
| SYSTOLIC BLOOD PRESSURE (<90 mmHg) | 120 | 03/14/05 14:37:00 | NO | +0 |
| APICAL HEART RATE (≥ 125 BPM) | 120 | 03/14/05 15:42:00 | NO | +0 |
| BUN (≥ 30 MG/DL) | 20 | 03/14/05 15:07:00 | NO | +0 |
| SODIUM (> 130 mmol/L) | 135 | 03/14/05 15:02:00 | NO | +0 |
| GLUCOSE LEVEL (≥ 250 MG/DL) | 100 | 03/14/05 15:32:00 | NO | +0 |
| pO2 ART (> 60 mmHg) | 65 | 03/14/05 15:02:00 | NO | +0 |
| TEMPERATURE (< 35° C OR > 40° C) | 37.1 | 03/15/05 15:08:00 | NO | +0 |
| pH ART (< 7.35) | 7.40 | 03/14/05 15:02:00 | NO | +0 |
| HEMATOCRIT (< 30%) | 25 | 03/16/05 08:58:08 | YES | +10 |
| PLEURAL EFFUSION | | | ○ YES ⊙ NO | +0 |
| NEOPLASTIC DISEASE | | | ○ YES ⊙ NO | +0 |
| LIVER DISEASE | | | ○ YES ⊙ NO | +0 |
| CONGESTIVE HEART FAILURE | ACTIVE PROBLEM: CONGESTIVE HEART FAILURE | | ⊙ YES ○ NO | +10 |
| RENAL DISEASE | | | ○ YES ⊙ NO | +0 |
| ALTERED MENTAL STATUS | | | ○ YES ⊙ NO | +0 |
| NURSING HOME RESIDENT | | | ○ YES ⊙ NO | +0 |
| CEREBROVASCULAR DISEASE | | | ⊙ YES ○ NO | +10 |

CALCULATED PNEUMONIA SEVERITY INDEX = 94

| PSI | CLASS | 30 DAY MORTALITY (%) | ORDER TO CONSIDER |
|---|---|---|---|
| <71 | I-II | <1 | CAP, AMBULATORY ORDER SET |
| 71-90 | III | <2.8 | CAP, ADMIT MED SURG ORDER SET |
| 191-130 | IV | 8.5 – 9.3 | CAP, ADMIT TO ICU ORDER SET |
| >130 | V | 27.0 – 31.1 | CAP, ADMIT TO ICU ORDER SET |

RESET   618 — SAVE PSI TO CHART   616 — ENTER ORDER   DONE

FIG. 6C.

USER INTERFACE FOR CLINICAL DECISION SUPPORT

CROSS-REFERENCE TO RELATED APPLICATIONS

This application claims the benefit of U.S. Provisional Application No. 60/827,594, filed Sep. 29, 2006. This application is also related by subject matter to the invention disclosed in the commonly assigned applications: U.S. application Ser. No. 11/623,589, filed on even date herewith, entitled "PROACTIVE AND INTERACTIVE CLINICAL DECISION SUPPORT;" and U.S. application Ser. No. 11/623,592, filed on even date herewith, entitled "CLINICAL DECISION SUPPORT TRIGGERED FROM ANOTHER CLINICAL DECISION SUPPORT." The disclosure of each of the aforementioned applications is hereby incorporated herein by reference in its entirety.

STATEMENT REGARDING FEDERALLY SPONSORED RESEARCH OR DEVELOPMENT

Not applicable.

BACKGROUND

The modern practice of medicine poses a number of challenges for clinicians to effectively deliver quality care to patients. In particular, the effective medical knowledge base continues to grow at a rapid pace, making it difficult for clinicians to keep up with and carry out recognized best practices. For instance, thousands of new journal articles are published each month providing a plethora of new evidence-based clinical information. Additionally, new drugs, treatment techniques, and testing procedures are continuously being researched and developed. The difficulty for clinicians to keep appraised of such information is exacerbated by the fact that clinicians are typically pulled in many different directions by a vast number of patients. Moreover, clinicians must often make quick decisions regarding patient treatment. As a result, there currently exists a gap between recognized best practices and actual clinician practices. This gap contributes to decreased quality of care, increased risk of medical errors, and increased cost of healthcare.

Over the past decade, there has been an increased use of computers to assist clinicians in the clinical care process. In particular, clinical decision support systems have been developed to address the gap between evidenced best practices and actual clinician practices by assisting clinicians in the delivery of care. Generally, clinical decision support systems may provide point-of-care case-specific clinical advice based on clinical information for a patient and a clinical knowledge base.

Different types of clinical decision support systems are available that may support various aspects of the clinical care process, such as clinical diagnosis and treatment planning, thereby advancing clinicians' use of best practices. In one form, currently available clinical decision support systems provide decision support through advice and alerts that are triggered based on stored clinical information. A clinical decision support system of this type monitors clinical information, such as information stored in a patient's electronic medical record, and compares the clinical information against a knowledge base, which may include different sets of algorithms and rules for providing decision support. When clinical information for a patient satisfies a rule or set of rules, an alert or other piece of advice is provided to a clinician.

However, this type of clinical decision support system provides only a reactive approach to decision support. Clinical advice is provided only if an existing condition is detected based on available clinical information for a patient. Clinicians may not use this type of system to proactively evaluate patients' conditions and develop treatment plans. Moreover, a particular rule is triggered and advice is provided only if clinical information required for the rule is stored and available to the system. For example, a rule may require ten pieces of clinical information to determine whether an alert should be provided. If only nine pieces of clinical information are available to the system, a determination for the rule cannot be made. Another shortcoming of this type of clinical decision support system is that it relies solely upon objective information to provide decision support. However, many clinical decisions require consideration of subjective factors.

In another form, currently available clinical decision support systems may operate as collection devices to gather clinical information from clinicians for decision support. This type of clinical decision support system provides an interactive approach as it solicits clinical information regarding a patient from a clinician and uses the solicited information to navigate through decision trees and generate clinical advice. However, this type of clinical decision support system is typically provided as a stand-alone system and is not tied to stored clinical information, such as information stored by an electronic medical record. Accordingly, the system does not automatically monitor clinical information and determine when a particular condition is present and/or a particular clinical action may be appropriate. Instead, a clinician must manually select and walk through a clinical decision support event. Additionally, a clinician must manually provide all clinical information used by the system. This may require the clinician to manually look-up clinical information, such as laboratory testing results, which may be a time-consuming process.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to providing proactive and interactive clinical decision support to assist a clinician in making decisions about a patient. When a clinical decision support event is triggered (either automatically or manually in various embodiments), stored clinical information available for a patient that is relevant to the clinical decision support event is accessed, and a user interface is generated and presented to a user. The user interface includes a number of clinical information elements that are relevant to the clinical decision support event. The stored clinical information that was accessed is used to populate at least a portion of the clinical information elements. The user may enter user-provided clinical information associated with the patient by adding new clinical information or modifying the stored clinical information populated in the user interface. Clinical advice may be provided based on both the stored clinical information and the user-provided clinical information. In some embodiments, clinical information provided by a user during a first clinical decision support event may be used to initiate a second clinical decision support event of another type.

BRIEF DESCRIPTION OF THE SEVERAL VIEWS OF THE DRAWINGS

The present invention is described in detail below with reference to the attached drawing figures, wherein:

FIGS. 4A and 4B are illustrative screen displays showing a manually triggered clinical decision support event in accordance with an embodiment of the present invention;

FIGS. 5A and 5B are illustrative screen displays showing a clinical decision support event triggered based on a order in accordance with an embodiment of the present invention;

FIGS. 6A-6C are illustrative screen displays showing a clinical decision support event automatically triggered based on monitored clinical information in accordance with an embodiment of the present invention.

DETAILED DESCRIPTION

Figure 1:
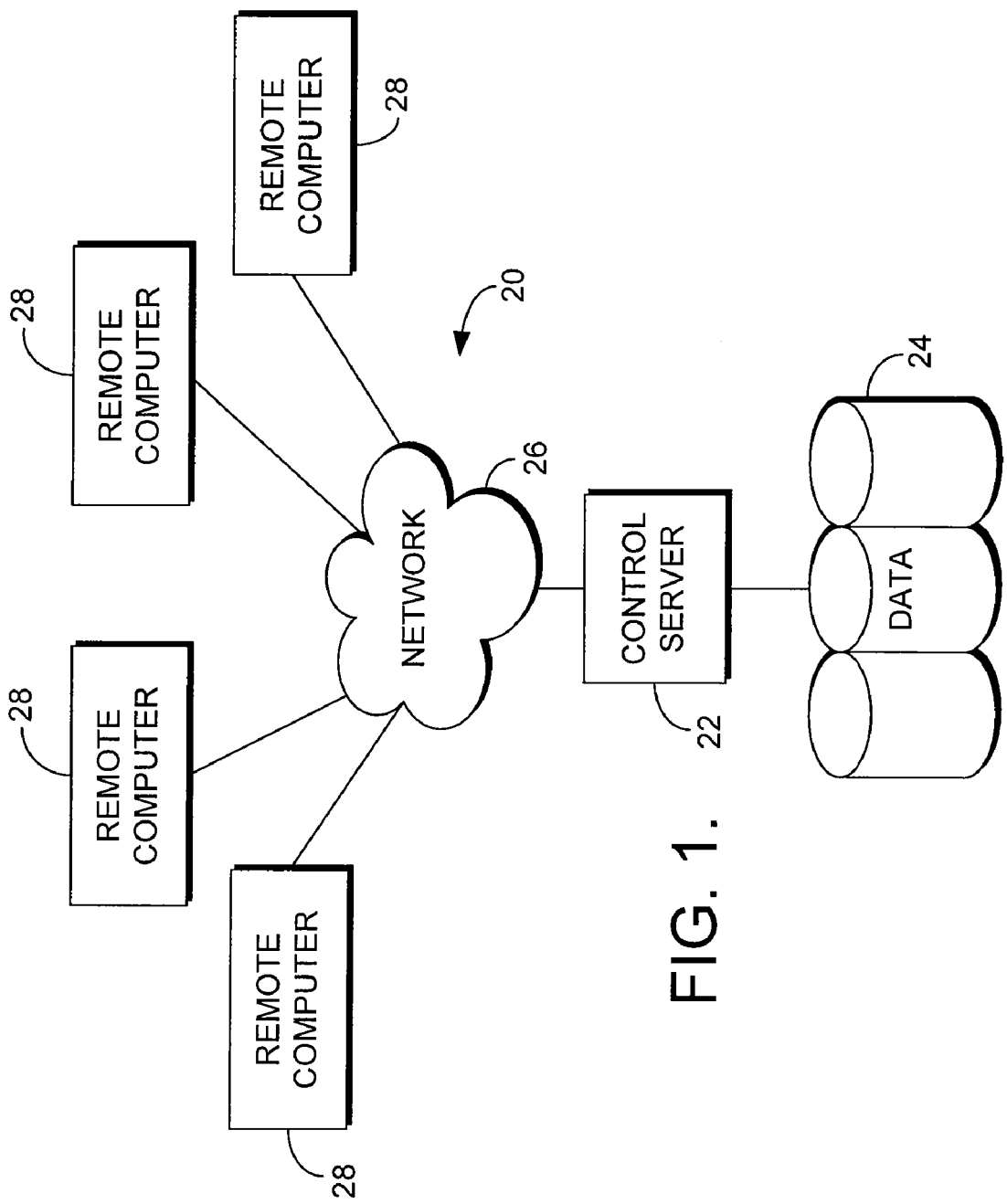
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods, systems, and user interfaces for providing clinical decision support in a proactive and interactive manner. A clinical decision support engine in accordance with an embodiment may match stored clinical information with a clinical decision support event, thereby presenting the stored clinical information to a clinician. The clinician may enter user-provided clinical information associated with the patient by adding new clinical information or modifying the stored clinical information that has been presented. Clinical advice is provided based on both the stored clinical information and the user-provided clinical information. Accordingly, embodiments of the present invention are capable of allowing clinicians to model a response by entering data in context of clinical information available from a data store. The interactive capabilities of the present invention increase patient safety by pushing the right clinical information at the right time to the right person, as well as letting the clinician interact and input data not captured in the system to determine the most relevant clinical scenario.

Embodiments of the present invention can positively impact health organizations' key imperatives in a variety of ways. Embodiments not only offer dramatic potential to improve patient safety, but also enable a healthcare organization with the ability to improve regulatory compliance while removing variance through the creation of individualized plans of care. Beyond the crucial focus on patient well-being, embodiments of the present invention assist in lowering costs to providers and organizations by increasing adherence with established clinical standards and ordering criteria. Embodiments present advantages over other decision support systems which are limited to data collection devices as clinical information is defaulted in the process, thereby streamlining the process and increasing efficiency.

Among other things, various embodiments of the present invention allow: relevant data to be pushed to clinicians at the time of execution allowing them to manipulate the data to assist in decision support of outcome improvements, treatment guidelines, and medication selection; interaction with a dynamic alert to determine a patient's specific clinical scenario; clinicians to examine various treatment scenarios by interacting with the clinical information; clinicians to place clinical orders directly from clinical decision support events; information captured during a clinical decision support event to be stored to track decision criteria; and links to the most up-to-date evidence-based information available.

Accordingly, in one aspect, an embodiment of the present invention is directed to a method in a clinical computing environment for providing clinical decision support. The method includes receiving a command to initiate a clinical decision support event associated with a patient. The method also includes accessing stored clinical information associated with the patient from a data store and generating a user interface for presentation using the stored clinical information. The user interface includes at least a portion of the stored clinical information. The method further includes presenting the user interface to a user and receiving user-provided clinical information from a user via the user interface. The method still further includes providing clinical advice based on the stored clinical information and the user-provided clinical information.

In another aspect of the invention, an embodiment is directed to a system in a clinical computing environment for providing a clinical decision support event. The system includes a knowledge base having one or more rules associated with one or more types of clinical decision support events. The system also includes an inference engine in communication with the knowledge base and a data store storing clinical information associated with a patient. The system further includes a user interface component that generates a user interface for a clinical decision support event. The user interface includes a number of clinical information elements relevant to the clinical decision support event. At least some of the clinical information elements are populated with clinical information accessed from the data store. The user interface is also configured to receive user-provided clinical information via the clinical information elements. The inference engine determines clinical advice based on the clinical information accessed from the data store and the user-provided clinical information received via the user interface. The clinical advice may then be provided in the user interface.

In a further aspect, an embodiment is directed to a method in a clinical computing environment for providing clinical decision support. The method includes accessing stored clinical information associated with a patient from a data store. The method also includes determining preliminary clinical advice based on the stored clinical information and presenting the stored clinical information and the preliminary clinical advice. The method further includes receiving user-provided clinical information and updating the clinical advice based on the stored clinical information and the user-provided clinical information.

Still another embodiment of the present invention is directed to a method in a clinical computing environment for providing clinical decision support. The method includes receiving a command to initiate a clinical decision support event associated with a patient. The method also includes accessing stored clinical information associated with the patient from a data store and determining clinical advice based on the stored clinical information. The method further includes generating a user interface for presentation using the stored clinical information and the clinical advice. The user interface includes a number of clinical information elements relevant to the clinical decision support event. At least a portion of the clinical information elements are populated with the stored clinical information and the clinical information elements are capable of being modified by a user. The method still further includes presenting the user interface to a user.

In another embodiment, an aspect of the invention is directed to a method in a clinical computing environment for providing a clinical decision support event associated with a patient, wherein the clinical decision support event has a number of relevant clinical information elements. The method includes monitoring stored clinical information associated with the patient. The method also includes determining that clinical information is not currently available for one or more of the clinical information elements relevant to the clinical decision support event. The method further includes initiating the clinical decision support event based on the stored clinical information. The method still further includes generating a user interface for the clinical decision support event. The user interface includes the clinical information elements relevant to the clinical decision support event. At least a portion of the clinical information elements is populated with the stored clinical information, and the clinical information elements are capable of being modified by a user. The method also includes presenting the user interface to a user.

Another embodiment of the present invention is directed to one or more computer-readable media having computer-useable instructions embodied thereon for presenting one or more user interfaces for facilitating a clinical decision support event. The user interface includes a clinical information area having a number of clinical information elements, wherein at least a portion of the plurality of clinical information elements are populated with stored clinical information associated with a patient. The clinical information elements are also configured to receive user-provided clinical information associated with the patient. The user interface also includes a clinical advice area for presenting clinical advice based on the stored clinical information and the user-provided clinical information.

In another aspect, an embodiment is directed to a method of providing a clinical decision support event, the method being within a computer system having a graphical user interface including a display and an input device. The method includes presenting, on the display, a plurality of number of information elements relevant to the clinical decision support event. At least one of the plurality of clinical information elements is populated with stored clinical information associated with a patient, wherein the stored clinical information is accessed from a data store. The method also includes receiving user-provided clinical information via the input device, wherein the user-provided clinical information is received in at least one of the clinical information elements. The method further includes in response to receiving the user-provided clinical information, determining clinical advice and presenting the clinical advice on the display.

In yet another embodiment of the present invention, an aspect is directed to a method in a clinical computing environment for providing clinical decision support. The method includes receiving user-provided clinical information during a first clinical decision support event associated with a patient. The method also includes comparing the user-provided clinical information and stored clinical information associated with the patient against one or more rules for initiating one or more clinical decision support events. The method further includes determining that at least one rule associated with a second clinical decision support event has been satisfied. The method also includes initiating the second clinical decision support event by generating and presenting a user interface for the second clinical decision support event, the user interface including user-provided clinical information from the first clinical decision support event relevant for the second clinical decision support event and stored clinical information relevant for the second clinical decision support event. The method further includes receiving, via the user interface for the second clinical decision support event, further user-provided clinical information. The method still further includes providing clinical advice based on the further user-provided clinical information, the user-provided clinical information from the first clinical decision support event relevant for the second clinical decision support event, and the stored clinical information relevant for the second clinical decision support event.

In a further aspect, an embodiment of the present invention is directed to a method in a clinical computing environment for initiating a clinical decision support event. The method includes initiating a first clinical decision support event associated with a patient. The method also includes generating and presenting a user interface based on stored clinical information associated with the patient and relevant to the first clinical decision support event. The method further includes receiving user-provided clinical information via the user interface and comparing the user-provided clinical information in conjunction with stored clinical information associated with the patient against one or more rules for initiating one or more clinical decision support events. The method still further includes determining that at least one of the one or more rules has been satisfied for a second clinical decision support event and initiating the second clinical decision support event.

In still a further aspect of the invention, an embodiment is directed to a system in a clinical computing environment for providing clinical decision support for a patient. The system includes a knowledge base comprising one or more rules associated with one or more clinical decision support events. The method also includes an inference engine in communication with the knowledge base and a data store storing clinical information associated with the patient. The inference engine monitors the stored clinical information and user-provided information received during a first clinical decision support event and compares the stored clinical information and the user-provided information against the one or more rules in the knowledge base to determine that at least one rule has been satisfied for a second clinical decision support event, thereby initiating the second clinical decision support event, and wherein the inference engine provides clinical advice for the second clinical decision support event based on at least a portion of the stored clinical information, at least a portion of the user-provided information received during the first clinical decision support event, and further user-provided information received during the second clinical decisions support event.

Referring now to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnections are well known. Accordingly, additional details concerning the internal construction of the server 22 and the remote computers 28 are not further disclosed herein.

Figure 2:
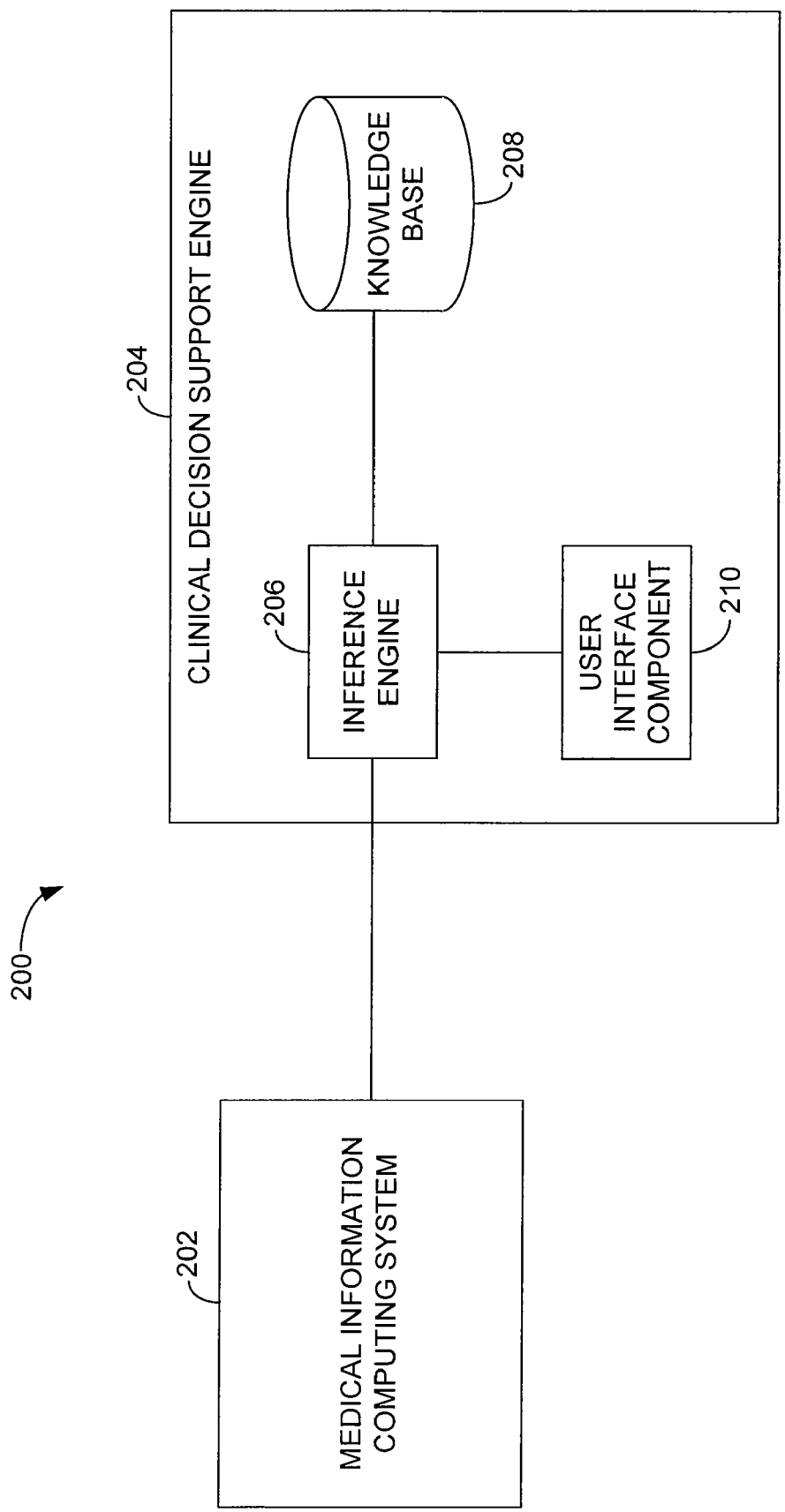
FIG. 2 is a block diagram of an exemplary system including a clinical decision support engine in accordance with an embodiment of the present invention.

Referring now to FIG. 2, a block diagram is provided illustrating an exemplary system 200 in which a clinical decision support engine 204 is shown interfaced with a medical information computing system 202 in accordance with an embodiment of the present invention. The medical information computing system 202 may be a comprehensive computing system within a clinical environment similar to the exemplary computing system 20 discussed above with reference to FIG. 1.

The clinical decision support engine 204 is generally configured to provide clinical decision support events to provide clinical advice to clinicians. As shown in FIG. 2, the clinical decision support engine 204 may include an inference engine 206, a knowledge base 208, and a user interface component 210. The inference engine 206 is configured to access clinical information from a data store, such as a data store within the medical information computing system 202, for clinical decision support events. Additionally, the inference engine 206 communicates with the knowledge base 208, which contains rules and rule sets associated with different types of clinical decision support events. The rules and rule sets may be based on available literature and best published evidence (e.g., medical, clinical, operational, and other guidelines, trade magazines, and the like), and may include, for example, medication usage criteria, complex decision trees, patient scoring systems, and clinical calculators. The clinical decision support engine further includes a user interface component 210, which provides for interactive clinical decision support events (which will be described in further detail below).

Although the clinical decision support event 204 is shown in FIG. 2 as being interfaced with the medical information computing system 202, one skilled in the art will recognize that in embodiments, the clinical decision support engine 204 may be integrated into the medical information computing system 202. In other embodiments, the clinical decision support engine 204 may simply be interfaced with a data store containing clinical information independent of a comprehensive medical information computing system. However, by interfacing and/or integrating the clinical decision support engine 204 with a comprehensive medical information computing system, such as the medical information computing system 202 of FIG. 2, a number of advantages may be realized. For example, the medical information computing system 202 may be interfaced with or otherwise include computing devices and/or computing systems in a variety of different clinical domains within a healthcare environment.

By way of example only and not limitation, the medical information computing system 202 may include a clinical laboratory system, a pharmacy system, a radiology system, and a hospital administration system. Accordingly, the medical information computing system 202 provides a unified computing architecture that is able to access and aggregate clinical information from a variety of different clinical domains and make the clinical information available to the clinical decision support engine 204. In an embodiment, the medical information computing system 202 may store clinical information from different clinical domains in a patient-centric electronic medical record.

Another advantage of interfacing and/or integrating the clinical decision support engine 204 with the medical information computing system 202 is that clinical decision support may be provided at the point-of-care via a remote computer. For instance, the medical information computing system 202 may include a number of remote computers, such as the remote computes 28 of FIG. 1. The remote computers may be located at, for example, patients' bedsides, nurses' stations, and physicians' offices. Accordingly, clinicians may be able to access the clinical decision support engine 204 via a remote computer of the medical information computing system 202, such that clinical decision support may be provided at the point-of-care.

In some embodiments, the medical information computing system 202 may include a computerized physician order entry (CPOE) system. A CPOE system allows clinicians to enter healthcare orders, which comprise requests for medication and non-medication tasks to be performed for a patient. An order may include, for instance, a request for a procedure, a medication, a laboratory test, an evaluation, a treatment, or a nursing task to be performed. In such embodiments, another advantage of interfacing and/or integrating the clinical decision support engine 204 with the medical information computing system 202 is that orders may be entered by a clinician directly from a clinical decision support event based on clinical advice provided by the clinical decision support engine 204.

A further advantage of interfacing and/or integrating the clinical decision support engine 204 with the medical information computing system 202 is that information associated with a decision support event may be captured and stored by the medical information computing system 202 with other clinical information, such as, for instance, in a patient's electronic medical record. For example, information that may be captured from a clinical decision support event may include clinical information entered by a clinician during the clinical decision support event, clinical advice determined during the decision support event, and any orders entered based on the decision support event.

Figure 3:
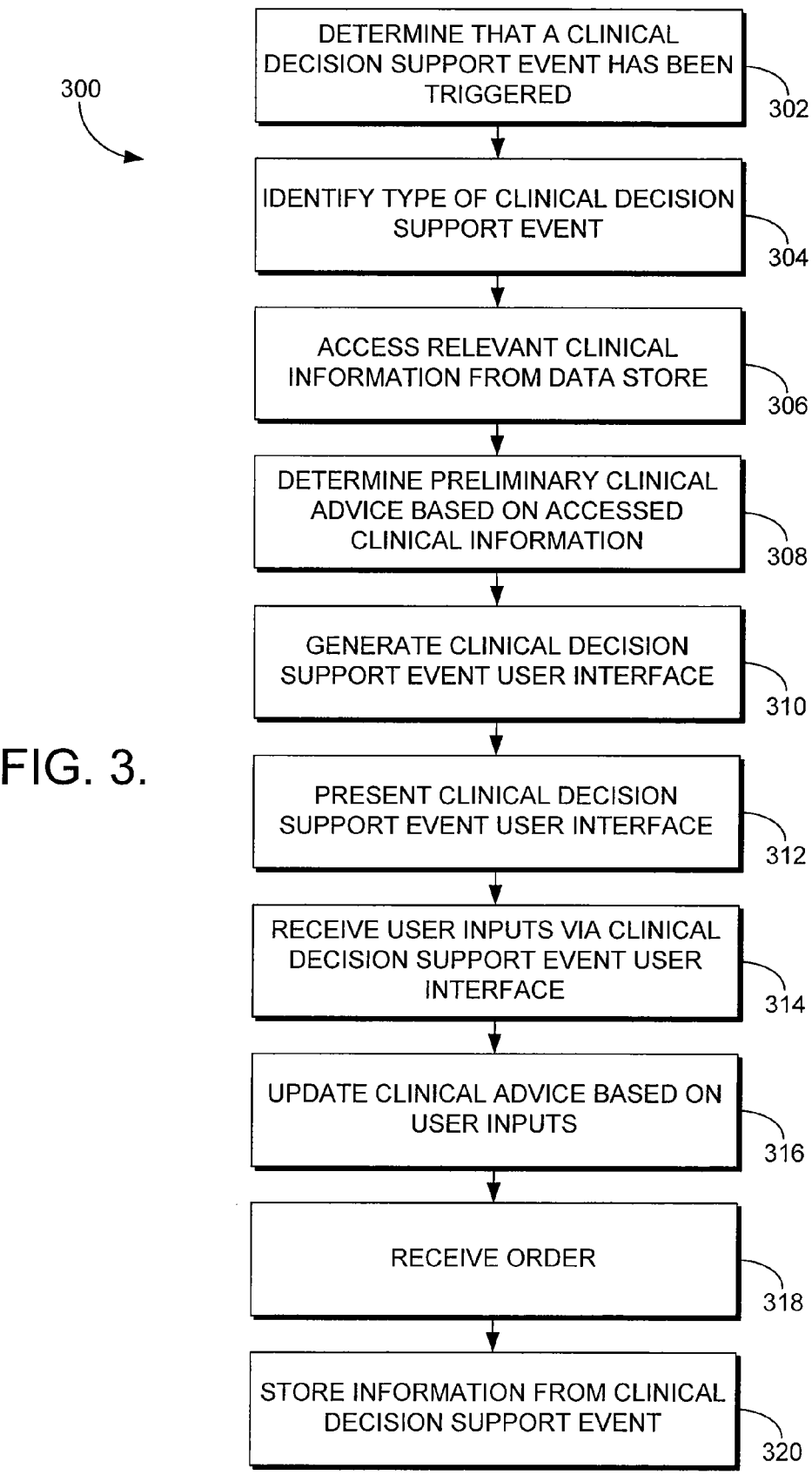
FIG. 3 is a flow diagram showing an exemplary method for providing a clinical decision support event in accordance with an embodiment of the present invention.

Turning now to FIG. 3, a flow diagram is provided illustrating a method 300 for providing an interactive decision support event in accordance with an embodiment of the present invention. Initially, as shown at block 302, the clinical decision support engine determines that a clinical decision support event has been triggered. A clinical decision support event may be triggered in a variety of different manners within the scope of the present invention. For instance, in one embodiment, a clinical decision support event may be triggered manually when a clinician selects a particular type of clinical decision support event. By way of example, a clinician may be concerned that patient may be susceptible to pneumonia. Accordingly, the clinician may request a clinical decision support event to examine the pneumonia severity index for the patient, which provides an indication regarding the patient's risk of pneumonia.

In another embodiment, a clinical decision support event may be triggered automatically based on an order entered by a clinician in a CPOE. For instance, hospitals may be concerned that clinicians are over-prescribing certain medications and may wish to have a verification process in place to ensure that medications are properly prescribed. As a specific example, Xigris® is a medication used to treat sepsis but provides only marginal effectiveness at a very high cost per dose. Additionally, Xigris® may result in adverse effects that present a high risk of causing patient death. Based on these characteristic, hospitals often wish to ensure that Xigris® is prescribed only in appropriate cases. To provide this verification process, the clinical decision support engine could be configured to automatically trigger a clinical decision support event whenever an order is placed for Xigris®.

In a further embodiment, the clinical decision support engine may monitor clinical information and automatically initiate a clinical decision support event when one or more rules associated with the clinical decision support event have been triggered. In this embodiment, the clinical decision support engine monitors clinical information for a particular patient. In embodiments in which the clinical decision support engine is interfaced with and/or integrated into a medical information computing system, the clinical decision support engine may monitor all clinical information collected by the medical information computing system for the patient. For instance, the medical information computing system may maintain an electronic medical record for the patient, and the clinical decision support engine may monitor the clinical information in the electronic medical record. In other embodiments, the clinical decision support engine may include or otherwise be associated with a data store other than that integrated with a comprehensive medical information computing system and may access clinical information in the data store.

Clinical decision support events may be automatically triggered in some embodiments of the present invention even when only partial clinical information for the clinical decision support is available in a data store accessible by the clinical decision support engine. Accordingly, embodiments of the present invention provide a significant advantage over other types of clinical decision support systems that provide alerts and/or clinical advice based on available clinical information. As previously mentioned, these types of clinical decision support systems provide a reactive approach as alerts and/or clinical advice may be provided only when all clinical information required for a rule is available. In contrast, embodiments of the present invention provide a proactive approach by being able to trigger clinical decision support events based on only limited clinical information. To provide an illustrative example, a pneumonia severity index (PSI) score is often used by clinicians to determine individual patients' risks of pneumonia. Depending on a patient's PSI score, clinical action may be advisable. In reactive-type clinical decision support systems, an alert may be automatically provided when a patient's PSI score reaches a predetermined level based on stored clinical information. However, if certain elements of clinical information are missing, the reactive-type system may not be able to calculate a PSI score or may calculate a misleadingly low PSI score that does not trigger an alert. In contrast, embodiments of the present invention may evaluate available clinical information and automatically trigger a clinical decision support event if it determines that further clinical information may indicate a risk of pneumonia. In other words, although a PSI score calculated by the clinical decision support engine does not indicate a risk of pneumonia or that any clinical action is currently advisable, the clinical decision support engine may recognize that certain elements of clinical information are missing and, if supplied by a clinician, may indicate a higher risk of pneumonia and that clinical action is advisable. Accordingly, the clinical decision support engine would automatically initiate a clinical decision support event.

After determining that a clinical decision support event has been triggered, the clinical decision support engine identifies the type of clinical decision support event, as shown at block 304. A variety of different types of clinical decision support events may be supported by embodiments of the present invention. By way of example only and not limitation, a clinical support event could be associated with the following: absolute neutrophil count, adult asthma management, pediatric asthma classification, DVT prophylaxis risk, pneumonia severity index scoring, rapid response team initiation, sepsis, glycemic control, and total parental nutrition. One skilled in the art will recognize that a wide variety of other types of clinical decision support events may be also supported by embodiments of the present invention.

The type of clinical decision support event is typically dependent on what triggers the clinical decision support event. For example, when a clinician manually selects a clinical decision support event, the selection specifies the particular type of event. For example a clinician may manually select a pneumonia severity index clinical decision support event or a sepsis clinical decision support event. When a clinical decision support event is triggered based on an order entered by a clinician, the type of clinical decision support associated with the order is identified. When a clinical decision support event is automatically triggered by one or more rules based on stored clinical information, the type of clinical decision support event associated with the one or more rules that triggered the event is identified.

As shown at block 306, clinical information is accessed for the clinical decision support event. The clinical information may be accessed, for instance, from one or more data stores either associated with or independent of a comprehensive medical computing system, such as the comprehensive medical computing system 202 of FIG. 2. Typically, only clinical information relevant for the clinical decision support event is accessed. For instance, a patient's electronic medical record may contain a wide variety of clinical information associated with the patient, much of which is not relevant for the clinical decision support event at hand. In some embodiments, the type of clinical decision support will dictate which elements of clinical information are relevant.

In some embodiments, such as that shown in FIG. 3, the clinical decision support engine determines preliminary clinical advice based on the accessed clinical information. As shown at block 308, the accessed clinical information is compared against one or more rules, for instance, rules stored in a knowledge base, such as the knowledge base 208 of FIG. 2, to determine clinical advice for the clinical support event, as shown at block 308. The one or more rules used to determine the clinical advice are associated with the type of clinical decision support event. The preliminary clinical advice may include one or more recommended clinical actions. In some cases, however, the preliminary clinical advice may be to do nothing.

Using the accessed clinical information and any preliminary clinical advice, a user interface may be generated, as shown at block 310. The user interface provides an interactive clinical decision support event by presenting relevant clinical information and clinical advice to a clinician while soliciting additional clinical information from the clinician and/or allowing the clinician to modify accessed clinical information. In particular, the user interface may include a variety of clinical information elements that are relevant to the type of clinical decision support event. Available clinical information that was accessed is used to populate corresponding clinical information elements. Often, however, clinical information will not be available for all clinical information elements. As such, clinical information elements for which clinical information was not available are left empty and/or unanswered in the user interface. For instance, in some cases, some clinical information elements may correspond with clinical information that is not typically stored, such as a subjective determination by a clinician. In other cases, clinical information elements typically stored may simply not be available for the patient (e.g., laboratory testing values if laboratory tests have not yet been conducted for the patient).

The user interface is next presented to a clinician, as shown at block 312. The user interface may be presented in any manner known in the art, such as, for example, visually via a monitor or other display device and/or audibly via speakers. The clinician may review the user interface, noting clinical information that was accessed for the clinical decision support event and any preliminary clinical advice determined based on the available clinical information.

After reviewing the information, the clinician may decide to interact with the user interface via one or more input devices and techniques known in the art, such as a mouse, a keyboard, a touchpad screen, and/or a microphone, for instance. Accordingly, at block 314, the clinical decision support engine receives user inputs via the user interface. In some cases, the clinician may add clinical information to clinical information elements for which stored clinical information was unavailable. For instance, a clinician may carry out a clinical decision support event while visiting with a patient. The clinician may ask the patient questions or otherwise examine the patient to acquire additional clinical information and enter the clinical information via the user interface. Alternatively or additionally to providing new clinical information, the clinician may modify clinical information elements pre-populated with stored clinical information. In some cases, a clinical decision support event may be based on a complex decision tree. When a clinician provides or modifies clinical information via the user interface, different paths of the decision tree may be followed with different clinical information elements being relevant. In such cases, the user interface may be modified to include new clinical information elements that become relevant based on user input provided via the user interface.

As shown at block 316, after receiving one or more user inputs via the user interface, the clinical advice is updated (or clinical advice is provided if preliminary clinical advice was not previously determined) based on the new or modified clinical information. As such, by soliciting additional or modified clinical information via the user interface, the clinical decision support engine may provide accurate clinical advice based on both stored clinical information and user-provided clinical information. Additionally, the clinician may employ the user interface to determine what clinical actions would be appropriate based on different hypotheticals. In other words, embodiments of the present invention allow clinicians to model different clinical scenarios by changing clinical information in different clinical information elements to determine the corresponding clinical advice for the different scenarios. For example, a clinician way wish to view clinical advice associated with various potential changes to a patient's condition. To do so, the clinician may simply modify clinical information in the user interface to represent different scenarios of potential changes in the patient's condition. As another example, some data elements may be associated with laboratory testing results that are not available (e.g., testing has not been ordered or testing has been ordered but not performed yet). The clinician, however, may wish to view clinical advice corresponding with different potential results. Accordingly, the clinician could enter different values in the user interface to view clinical advice corresponding with the different values.

In embodiments in which the clinical decision support engine is interfaced with a CPOE, a clinician may enter an order from the clinical decision support event, as shown at block 318. For example, the clinical advice may recommend one or more clinical actions, such as prescribing a medication for a patient or requesting a laboratory test to be performed. Accordingly, the clinician may enter the appropriate order based on the clinical advice from the clinical decision support engine. In some embodiments, the user interface for the clinical decision support event may include an area for the clinician to enter one or more orders. In other embodiments, the clinician may be navigated from the clinical decision support event directly to the CPOE system to enter any orders.

While orders entered by a clinician are typically based on clinical advice provided by the clinical decision support event, the clinician may chose to enter additional or different orders. In some cases, by reviewing the user interface for the clinical decision support event, the clinician may recognize that further clinical information is desirable to provide a more complete clinical decision support event. For instance, the clinician may recognize that further laboratory testing would provide vital results that may have a significant impact on the clinical advice. In such an event, the clinician may place an order for the laboratory testing from the clinical decision support event.

In some cases, a clinician may wish to save information associated with a clinical decision support event. For example, such information may provide support for a clinician's decision to pursue a particular course of patient treatment. Accordingly, as shown at block 320, information associated with the clinical decision support event is stored. In some embodiments, the information stored may be the clinical advice provided by the clinical decision support event and the clinical information (both accessed and clinician provided) used to determine the clinical device. In some embodiments, clinical information provided by a clinician during the clinical decision support event may be stored with other clinical information for the patient, such as in the patient's electronic medical record. In some cases, clinical information in a patient electronic medical record may be modified by clinical information provided during the clinical decision support event.

In operation, an example of a manually triggered clinical decision support event will now be described with reference to FIGS. 4A-4B, which include screen displays illustrating user interfaces for a clinical decision support event in accordance with an embodiment of the present invention. The present example is related to a clinical decision support event for selecting B-cell deficiency testing. A B-cell is a type of lymphocyte (i.e., white blood cell) that is involved in the production of antibodies for immune responses. There are a wide variety of tests associated with B-cell deficiency, and the appropriate test(s) for a given patient depends upon a number of different variables. Because of this complexity (e.g., number of different tests and variables for selecting appropriate tests), most clinicians need some form of assistance in selecting appropriate testing for B-cell deficiency. Accordingly, a clinical decision support event may be provided to assist clinicians with the selection of B-cell deficiency test(s).

In the present example, a clinician is reviewing a patient's electronic medical record and is concerned that the patient has B-cell deficiency. Accordingly, the clinician manually selects a clinical decision support event for B-cell deficiency testing.

Based on the clinician's selection, clinical information relevant for the clinical decision support event is accessed from the patient's electronic medical record. Using the available data, the clinical decision support engine develops preliminary clinical advice regarding which test(s) should be ordered. Additionally, the clinical decision support engine generates and presents a user interface using the accessed clinical information and preliminary clinical advice.

Referring to FIG. 4A, a screen display is provided showing the user interface 400 generated for the B-cell deficiency clinical decision support event of the present example. The clinical decision support event user interface 400 generally includes a patient information area 402, a clinical information area 404, a clinical advice area 406, and an order entry area 408. General patient information is provided in the patient information area 402 to indicate the current patient being evaluated. The clinical information area 404 includes the clinical information elements relevant to the clinical decision support event. As shown in FIG. 4A, clinical information accessed from the patient's electronic medical record has been populated in some of the clinical information elements of the clinical decision support event user interface 400. For example, a laboratory result value has been indicated for the clinical information element "Serum Levels of IgA" 410. However, clinical information was not available in the electronic medical record for all clinical information elements. For instance, a "Result Not Found" indication has been provided for the clinical information element "Partial Ig- and B-cell-deficiency phenotypes" 412.

The clinical advice area 406 presents an indication of clinical advice for the clinical decision support event. As shown in the clinical advice area 406 of FIG. 4A, preliminary advice has been provided based on the clinical information accessed from the patient's electronic medical record. In particular, no tests are recommended for the patient.

The clinician may review the clinical information elements and determine whether any additional clinical information may be provided or if any clinical information pre-populated in the clinical information element area 404 may be modified. In the present example, the clinician recognizes that a clinical information element "Enlarged lymph nodes and tonsils" 414 has been defaulted to "No." However, the clinician has just examined the patient and detected enlarged lymph nodes and tonsils. Accordingly, the clinician changes the clinical information for the element 414 to a "Yes," as shown in the clinical decision support event user interface of FIG. 4B. Based on the clinician's input, the clinical advice has been updated. In particular, the clinical advice area 406 now indicates that the recommended tests include "AICDA (HIGM2)," and "UNG."

The order entry area 408 of the clinical decision support event user interface 400 provides a convenient way for the clinician to enter an order based on the clinical decision support event. The order entry area 408 includes the B-cell deficiency tests that may be ordered. The clinician may simply review the clinical advice provided by the clinical decision support event and select an order for the tests the clinician wishes to have performed for the patient. Here, the clinician has selected an order for an "AICDA" test 416 and an order for a "UNG" test 418. In some embodiments, the orders may be automatically entered in response to the clinician's selection in the clinical decision support event user interface 400. In other embodiments, the selections in the clinical decision support event user interface 400 allow the clinician to access a CPOE system and enter any necessary order details to complete the order.

Referring now to FIGS. 5A-5B, screen displays are provided illustrating an exemplary clinical decision support event automatically triggered when an order is entered by a clinician. The present example illustrates a clinical decision support event for validating a medication order for Xigris®. As discussed previously, Xigris® is a medication prescribed for sepsis but has a high cost per dose, marginal effectiveness, and a high risk of adverse affects that may result in patient death.

In the present example, when a clinician enters an order for Xigris®, a clinical decision support event is automatically triggered. The clinical decision support engine accesses relevant clinical information and generates preliminary clinical advice based on that data. In particular, the clinical advice is directed towards whether Xigris® should be ordered for the patient. A user interface, such as the clinical decision support event user interface 500 shown in FIG. 5A, is generated based on the accessed data and preliminary clinical advice and presented to the clinician. As shown in FIG. 5A, the clinical decision support event user interface 500 generally includes a patient information area 502, a clinical information area 504, a clinical advice area 506, and an order entry area 508.

The patient information area 502 includes general patient information to identify the patient being evaluated. The clinical information area 504 includes the clinical information elements relevant to the clinical decision support event. The clinical information elements have been populated using the accessed clinical information for the patient. However, any clinical information elements for which clinical information was not available are left open (or may be defaulted to "No").

Based on the available clinical information, the clinical decision support engine has determined that Xigris® should not be ordered for the patient. In particular, the preliminary clinical advice provided in the clinical advice area 506 includes: "Do NOT order Xigris. Patient does not meet criteria as defined." As the clinician reviews the clinical information presented in the clinical information elements of the user interface 500, the clinician recognizes that the clinical information element 510, which includes: "Does the patient have a syndrome with a high risk of associated infection," has "No" as the associated clinical information. The clinician recognizes that this is incorrect and changes the clinical information for the element 510 to "Yes," as shown in FIG. 5B. In response to the clinician's input, the clinical advice is updated to indicate: "Criteria met for Xigris order; please continue by verifying that no contraindications are present."

The clinician now refers to the order entry area 508 and selects the "Continue ordering Xigris" option 512. The clinician may then be returned to the CPOE system at which the order was initiated and continue to enter and complete the Xigris® order.

An example of an embodiment of the present invention in which a clinical support event is automatically triggered by one or more rules based on monitored clinical information will now be described with reference to FIGS. 6A-6C. The present example is directed to a PSI clinical decision support event. As mentioned previously, clinicians often calculate PSI scores for patients to determine risk of pneumonia. The clinical decision support engine may monitor clinical information and calculate a PSI score based on available data. When a determination is made that a patient has a predetermined risk for pneumonia, a clinical decision support event is automatically triggered. For instance, the clinical decision support engine may make the determination to trigger the event by calculating a score indicating a risk based on available clinical information and/or by determining that if additional clinical information were provided, a score may be calculated that indicates a risk.

After the clinical decision support event has been automatically triggered, a user interface is generated and presented to a clinician. Referring to FIG. 6A, a screen display is provided illustrating an exemplary user interface 600 for the PSI clinical decision support event of the present example. As shown in FIG. 6A, the user interface generally includes a patient information area 602, a clinical information element area 604, and a clinical advice area 606.

As in previous examples, the patient information area 602 provides a general indication of the present patient. Additionally, clinical information accessed from a data store is provided in clinical information elements of the clinical information element area 604. The clinical advice area 606 includes a preliminary PSI score that has been calculated based on the stored clinical information. Additionally, the clinical advice area 606 includes a table showing ranges of PSI score with a corresponding class, 30-day mortality, and order that the clinician may wish to consider. In the present example, a PSI score of 84 has been calculated based on stored clinical information for the patient. Accordingly, the information 608 corresponding with this score has been highlighted in the table within the clinical advice area 606. In particular, the PSI score falls in the range from 71-90, indicating a class III score with a <2.8% 30-day mortality, and a recommended order of "CAP, Admit Med. Surg. Order Set."

Clinical decision support event user interfaces of embodiments of the present invention may include links to evidence-based information regarding the particular clinical decision support event. Such information can be particularly useful to clinicians by providing the clinicians with context and supporting evidence-based information for the clinical decision support event. For instance, the user interface 600 of FIG. 6A includes a link 610 that allows a user to access information regarding the PSI. After reviewing the user interface 600, the clinician may select the link 610, causing the presentation of the information shown in the screen display 612 of FIG. 6B.

After reviewing the user interface 600 and any evidence-based information, such as that shown in FIG. 6B, the clinician may choose to add and/or modify clinical information in the user interface. In the present example, the clinician recognizes that the patient has cerebrovascular disease but the corresponding clinical information element 614 has been defaulted to "No" in the user interface 600 of FIG. 6A. As shown in FIG. 6C, the clinician selects "Yes" for the "Cerebrovascular disease" clinical information element 614 in the user interface 600, which results in a new PSI score to be calculated. The new PSI score is reflected in the clinical advice area 606, and in the present example, the new score falls in a different range, indicating a different order set to be recommended. In particular, the PSI score now falls in the range from 91-130, indicating a class IV score with a 8.5%-9.3% 30-day mortality, and a recommended order of "CAP, Admit to ICU Order Set."

Based on the clinical decision support event, the clinician may choose to enter an order for the patient (e.g., using button 616). Additionally, the clinician may choose to save the PSI score and/or information used to calculate the PSI score to the patient's electronic medical record. For instance, the clinician may select the "Save PSI to Chart" button 618 to save information associated with the clinical decision support event.

Figure 7:
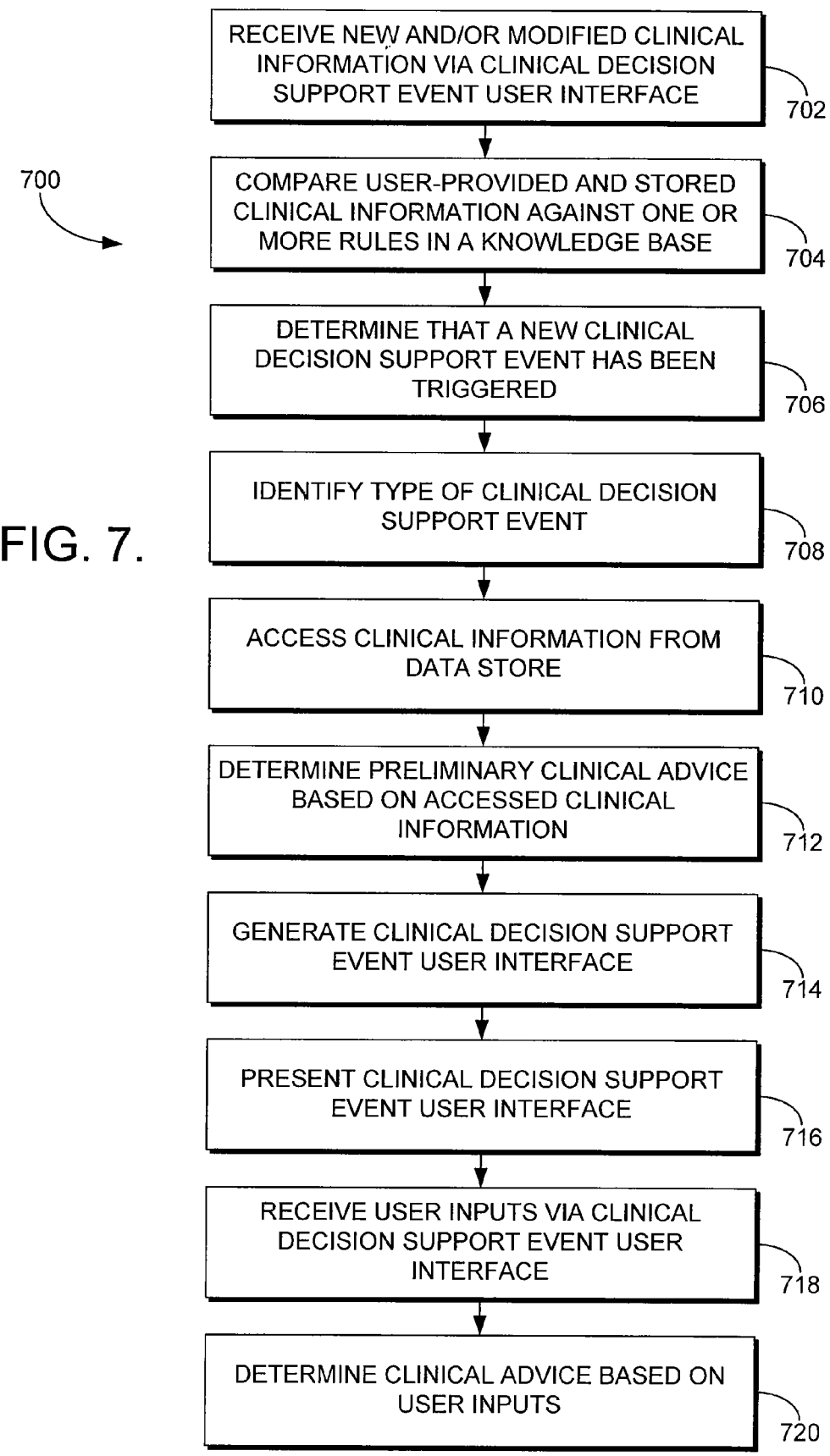
FIG. 7 is a flow diagram showing an exemplary method for providing a new clinical decision support event based on clinical information provided during another clinical decision support event in accordance with an embodiment of the present invention.

In a further embodiment of the present invention, clinical information provided by a clinician during a clinical decision support event may automatically trigger a new clinical decision support event. With reference to FIG. 7, a flow diagram is shown illustrating a method 700 for providing a new clinical decision support event based on clinical information provided by a clinician during another clinical decision support event. Initially, as shown at block 702, new and/or modified clinical information is received from a clinician via a user interface during a clinical decision support event. For instance, a clinical decision support event may have been automatically or manually triggered for a patient as described above for the method 300 with reference to FIG. 3. After reviewing clinical information elements in the user interface generated for the clinical decision support event, the clinician may decide to enter additional clinical information or modify clinical information in the user interface.

After receiving new and/or modified user-provided clinical information via the user interface, the clinical decision support engine may compare all available clinician information against one or more rules in a knowledge base, as shown at block 704. In other words, the clinical decision support engine may compare the new and/or modified user-provided clinical information in conjunction with clinical information available in a data store to the one or more rules in the knowledge base.

Based on the comparison, a determination is made at block 706 that a new clinical decision support event has been triggered based on the user-provided and stored clinical information. In particular, the user-provided information in conjunction with stored clinical information has indicated that a different type of clinical decision support event is appropriate in addition to or in lieu of the previous clinical decision support event. As such, a new clinical decision support is initiated.

After the new clinical decision support has been initiated, a method similar to the method 300 described with reference to FIG. 3, may provide the new clinical decision support event. In particular, the type of clinical decision support event is identified at block 708. Relevant clinical information for the new clinical decision support event, including any relevant new and/or modified clinical information provided during the previous decision support event, is accessed, as shown at block 710. Preliminary clinical advice may then be determined based on the relevant clinical information, as shown at block 712. A user interface is generated using the relevant clinical information and any preliminary clinical advice, as shown at block 714. The user interface is then presented at block 716. The clinician may add and/or modify clinical information within the user interface, as shown at block 718. Based on any clinical information additions and/or modifications received via the user interface, the clinical advice is updated (or clinical advice is determined if no preliminary clinical advice was previously determined) and presented via the user interface, as shown at block 720.

As can be understood, the present invention provides systems, methods, and user interfaces for providing clinical decision support events in a computerized healthcare environment. Embodiments of the present invention may leverage clinical information available in a data store, such as a patient's electronic medical record, for clinical decision support events. Additionally, embodiments of the present invention provide an interactive approach by allowing users to add and/or modify clinical information used during clinical decision support events.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer-readable media having computer-useable instructions embodied thereon for presenting one or more user interfaces for facilitating a clinical decision support event, the one or more user interfaces comprising:
  a clinical information area having a plurality of clinical information elements, at least a first portion of the plurality of clinical information elements being populated with stored clinical information associated with a patient and a second portion of the plurality of clinical information elements requesting additional user-provided clinical information; and
  a clinical advice area for presenting clinical advice based on the stored clinical information and the additional user-provided clinical information,
  wherein the one or more user interfaces are presented in response to a determination that a clinical decision support event has been initiated, wherein the determination that the clinical decision support event has been initiated is based on a comparison of stored clinical information against one or more rules associated with the clinical decision support event and a determination that at least one of the one or more rules associated with the clinical decision support event has been satisfied based on the stored clinical information, wherein the one or more or more rules are satisfied when a determination is made that certain elements of clinical information for the clinical decision support event are missing, an analysis of the stored clinical information does not indicate that any clinical action is currently advisable, and that the clinical action could be advisable based on possible values for the certain elements that are missing.

2. The one or more non-transitory computer-readable media of claim 1, wherein the one or more user interfaces further comprise a patient information area for presenting patient identification information associated with the patient.

3. The one or more non-transitory computer-readable media of claim 1, wherein the one or more user interfaces further comprise a clinical order area for receiving one or more clinical orders for the patient.

4. The one or more non-transitory computer-readable media of claim 1, wherein the one or more user interfaces further comprise evidence-based medical information associated with the clinical decision support event.

5. The one or more non-transitory computer-readable media of claim 1, wherein at least a portion of the user-provided clinical information modifies at least a portion of the stored clinical information.

6. The one or more non-transitory computer-readable media of claim 1, wherein the one or more user interfaces further include an option to save the clinical advice given with the clinical decision support event.

7. The one or more non-transitory computer-readable media of claim 1, wherein the determination that the clinical decision support event has been initiated is based on a user command to initiate the clinical decision support event.

8. The one or more non-transitory computer-readable media of claim 1, wherein the determination that the clinical decision support event has been initiated is based on receipt of a clinical order and a determination that the clinical decision support event is associated with the clinical order.

9. The one or more non-transitory computer-readable media of claim 1, wherein the clinical advice area also presents preliminary clinical advice based on the stored clinical information, the preliminary clinical advice being updated to the clinical advice based on the stored clinical information and the user-provided clinical information.

10. A method of providing a clinical decision support event, the method comprising:
  generating, based on presently available information about a patient, a score for activating a particular clinical decision support event, wherein the score does not indicate that the particular clinical decision support event is advisable;
  determining that at least one item of clinical information that could change the score is missing from the presently available information about the patient;
  determining that the at least on item of clinical information, if provided, could change the score enough that the particular clinical decision support event is advisable;
  presenting, on a display, a plurality of clinical information elements relevant to the clinical decision support event, at least one of the plurality of clinical information elements being populated with stored clinical information associated with a patient, the stored clinical information being accessed from a data store, wherein the information elements are presented upon determining that the at least one item of clinical information, if provided, could change the score enough that the particular clinical decision support event is advisable;
  receiving user-provided clinical information via the input device, the user-provided clinical information being received in at least one of the plurality of clinical information elements; and
  in response to receiving the user-provided clinical information, determining, at the computing system, clinical advice and presenting the clinical advice on the display.

11. The method of claim 10, wherein the plurality of clinical information elements relevant to the clinical decision support event are displayed in response to a determination that the clinical decision support event has been initiated.

12. The method of claim 11, wherein the determination that the clinical decision support event has been initiated is based on a user command to initiate the clinical decision support event.

13. The method of claim 11, wherein the determination that the clinical decision support event has been initiated is based on receipt of a clinical order and a
  determination that the clinical decision support event is associated with the clinical order.

14. The method of claim 10, further comprising presenting, on the display, in conjunction with the plurality of clinical information elements relevant to the clinical decision support event, preliminary clinical advice determined based on the stored clinical information, wherein determining clinical advice comprises updated the preliminary clinical advice based on the user-provided clinical information.

15. The method of claim 10, further comprising saving the clinical advice given with the clinical decision support event in a data store for subsequent retrieval.

* * * * *